US008242160B2

(12) United States Patent
Weissman et al.

(10) Patent No.: US 8,242,160 B2
(45) Date of Patent: Aug. 14, 2012

(54) INHIBITORS OF UBIQUITIN E1

(75) Inventors: Allan M. Weissman, Bethesda, MD (US); Yili Yang, Montgomery Village, MD (US); Jane P. Jensen, Gettysburg, PA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 12/842,346

(22) Filed: Jul. 23, 2010

(65) Prior Publication Data
US 2010/0305180 A1 Dec. 2, 2010

Related U.S. Application Data

(60) Division of application No. 12/154,156, filed on May 19, 2008, now abandoned, which is a continuation-in-part of application No. PCT/US2006/045032, filed on Nov. 20, 2006.

(60) Provisional application No. 60/738,242, filed on Nov. 19, 2005.

(51) Int. Cl.
*A61K 31/4152* (2006.01)
(52) U.S. Cl. ...................................... 514/404
(58) Field of Classification Search ................. None
See application file for complete search history.

(56) References Cited

U.S. PATENT DOCUMENTS

2004/0220188 A1* 11/2004 Bombrun et al. ............. 514/249
2005/0112562 A1   5/2005 Payan et al.

FOREIGN PATENT DOCUMENTS

| WO | 02102359 A2 | 12/2002 |
|----|-------------|---------|
| WO | WO-02/102359 | 12/2002 |
| WO | 03073999 A2 | 9/2003 |
| WO | WO-03/074550 | 9/2003 |
| WO | WO-2004/043955 | 5/2004 |
| WO | WO-2005/041951 | 5/2005 |
| WO | WO-2005/076695 | 8/2005 |

OTHER PUBLICATIONS

Wang et al., J. Immunol. 2007, 179, pp. 5958-5965.*
Yang et al. Cancer Research 2007; 67: (19), Oct. 1, 2007.*
Kresser, Chris. How inflammation makes you fat and diabetic (and vice versa). Sep. 2010. Obtained from <http://chriskresser.com/how-inflammation-makes-you-fat-and-diabetic-and-vice-versa> [Accessed Jan. 31, 2012].*
Savoia et al. Clinical Science (2007) 112, pp. 375-384.*
Golub et al.; Science; vol. 286; pp. 531-536; (1999).
Huff, Joel R.; "HIV Protease: A Novel Chemotherapeutic Target for AIDS"; Journal of Medicinal Chemistry; 34(8); pp. 2305-2314; (1991).
Lala et al; Cancer and Metastasis Reviews; 17(1); pp. 91-106; (1998).
Morissette et al; "High-throughput Crystallization: Polymorophs, Salts, Co-crystals and Solvates of Pharmaceutical Solids"; Advancedf Drug Delivery Reviews; 56; pp. 275-300; (2004).
Vippagunta, Sudha R.; "Crystalline Solids"; Advanced Drug Delivery Reviews; 48; pp. 3-26; (2001).
Yang et al.; "Inhibitors of Ubiquitin-Activating Enzyme (E1), a New Class of Potential Cancer Therapeutics"; Cancer Research; 67:(19); pp. 9472-9481; (2007).
International Search Report; International Application No. PCT/US2006/045032; International Filing Date Nov. 20, 2006; Date of Mailing Jun. 6, 2007; 5 pages.
International Preliminary Report on Patentability; International Application No. PCT/US2006/045032; International Filing Date Nov. 20, 2006; Date of Issuance May 20, 2008; 8 pages.
Abraham, Edward; "Nuclear Factor-kB and Its Role in Sepsis-Associated Organ Failure"; Journal of Infectious Diseases; 187; pp. S364-S369; (2003).
Chiba, et al.; "A Selective NFkB Inhibitor, DHMEQ, Reduced Atherosclerosis in ApoE-deficient Mice"; Journal of Atherosclerosis and Thrombosis; 13; pp. 308-313; (2006).
Christman et al.; "Nuclear Factor Kappa B: A Pivotal Role in the Systemic Inflammatory Response Syndrome and New Target for Therapy"; Intensive Care Medicine; 24(11); pp. 1131-1138; (1998).
Fujimoto, et al.; "Inhibition of Nuclear Factor-KB in T Cells Suppresses Lung Fibrosis"; Am J Respir Crit Care Med; 176; pp. 1251-1260; (2007).
Kaltschmidt et al.; "Transcription Factor NF-KB is Activated in Microglia During Experimental Autoimmune Encephalomyelitis"; Journal of NeuroImmunology; 55(1); pp. 99-106; (1994).
Karin et al.; "The IKK NF-kB System: A Treasure Trove for Drug Development" Nature Reviews Drug Discovery; 3; pp. 17-26; (2004).
Koedel, et al.; "Pharmacologic Interference with NF-kappaB Activation Attenuates Central Nervous System Complications in Experimental Pneumococcal Meningitis"; J. Infect. Dis.; 182(5); pp. 1437-1445; (2000).
Maitra et al.; "Inhibitiion of NFKB by The Natural Product Withaferin A in Cellular Models of Cystic Fibrosis Inflammation"; Journal of Inflammation; 6:15; pp. 1-5; (2009).
Matsumori et al., "Suppression of Cytokines and Nitric Oxide Production, and Protection Against Lethal Endotoxemia and Viral Myocarditis by a New NF-kB Inhibitor"; The European Journal of Heart Failure 6; pp. 137-144; (2004).
Sakai, et al.; "p38 MAPK Phosphorylatioin and NF-KB Activation in Human Crescentic Glomerulonephritis"; Nephrol Dial Transplant; 17: pp. 998-1004 (2002).
Tripathi et al.; "NF-kB Transcription Factor: A Key Player in the Generation of Immune Response"; Current Science; 90(4); pp. 519-531; (2006).
Yamamoto, et al.; "Therapeutic Potential of Inhibition of the NF-KB Pathway in the Treatment of Inflammation and Cancer"; J. Clin Invest; 107(2) ; pp. 135-142; (2001).
Yanaba, et al.; "The Proteasome Inhibitor Bortezomib Inhibits T Cell-Dependent Inflammatory Responses"; Journal of Leukocyte Biology; 88, pp. 117-122 (2010).

* cited by examiner

*Primary Examiner* — Rebecca Anderson
*Assistant Examiner* — Alicia L Otton
(74) *Attorney, Agent, or Firm* — Cantor Colburn LLP

(57) ABSTRACT

The present invention features pyrazolidinyl compounds, pharmaceutical compositions of substituted pyrazolidinyl compounds and methods of treating a patient suffering from cancer or viral infection, the method comprising administering to a patient one or more pyrazolidinyl compounds of the invention.

3 Claims, 11 Drawing Sheets

Compounds
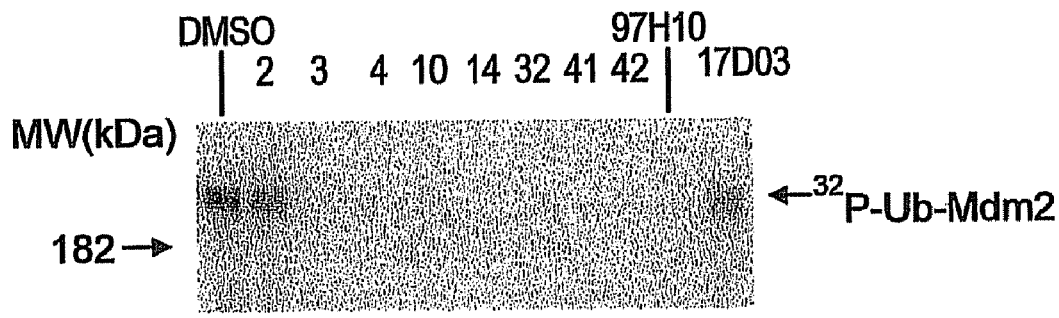
Hits from high throughput screening inhibit auto-ubiquitination of GST-Mdm2 *in vitro*.
FIG. 1A
Compounds
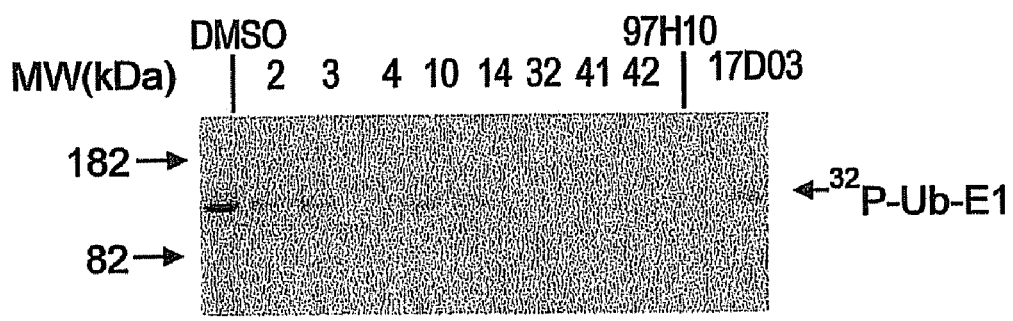
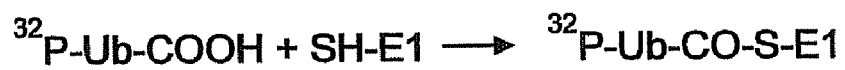
Some compounds inhibit the formation of E1-Ub complex *in vitro* In this assay labeled ubiquitin is being used to look at the high energy thiolester linkage between E1 and ubiquitin.
FIG. 1B

Some compounds inhibit both E1 and E2, whereas others selectively inhibit E2 only.

Without E1 preloading with Ub, E1-selective inhibitors can effectively prevent the formation of E2-Ub conjugates.

Cmpd 41 inhibits auto-ubiquitination of RING finger E3 Mdm2 and HECT domain E3 Nedd4 in vitro.

E1 restores compound 41-induced inhibition of Cyclin E degradation in S100.

Compound 41 inhibits TNF-induced IκBα degradation.

Compound 41 inhibits TNF-induced IκBα phosphorylation.

Cmpd 41 inhibits TNF-induced TRAF6 ubiquitination.

E1 inhibitor increases the level of Mdm2 and p53 in RPE cells.

p53 induced by cmpd 41 is transcriptional active.

E1 inhibitor induces growth arrest in untransformed RPE cells as measured by MTT assay.

Proteasome and E1 inhibitors kill mouse myeloma cells (J588) in a dose-dependent manner.

INHIBITORS OF UBIQUITIN E1

CROSS-REFERENCE TO RELATED APPLICATION

The present application is a divisional of U.S. patent application Ser. No. 12/154,156, filed on May 19, 2008, which is a continuation-in-part of International Application No. PCT/US06/45032 having an International filing date of Nov. 20, 2006, and which claims the benefit of U.S. provisional application No. 60/738,242, filed Nov. 19, 2005, all of which applications are incorporated herein by reference in its entirety.

GOVERNMENT SUPPORT

Research supporting this application was carried out by the United States of America as represented by the Secretary, Department of Health and Human Services.

BACKGROUND OF THE INVENTION

1. Field of the Invention

The present invention involves pyrazolidinyl compounds and methods and pharmaceutical compositions that comprise such compounds. Compounds of the invention can be effective to modulate the function of the ubitquitylation system, regulate p53 and Mdm2 stability and activity as well as to act as therapeutic agents in a variety of indications, particularly to treat cancer as well to treat viral infections, particularly to treat retroviral-infected mammalian cells.

2. Background

The development of cancer can depend on the accumulation of specific genetic alterations that allow aberrant cell proliferation, including growth of tumor cells. Protection from such aberrant growth is provided by several mechanisms that work by inducing apoptotic cell death in cells undergoing oncogenic changes. Therefore, for a tumor cell to survive, it must acquire genetic alterations that perturb the link between abnormal growth and cell death. The p53 tumor suppressor protein can induce apoptotic cell death and plays a pivotal role in tumor suppression. Wild type p53 functions as a transcriptional regulator to coordinately control multiple pathways in cell cycling, apoptosis, and angiogenesis.

Loss of the ability to induce p53 or other loss of p53 activity can lead to uncontrolled cell proliferation of the affected cells and tumor growth. In approximately 50% of human cancers, a wild type p53 gene is nevertheless retained. In such cancers, the defect that frequently occurs is a failure to stabilize and activate p53 to thereby prevent tumor development.

The Mdm2 protein plays an important role in targeting the degradation of p53 in normal cells to allow normal growth and development. In particular, inhibition of Mdm2 is required to allow activation of a p53 response. In tumors with wild type p53, defects can occur that lead to increased Mdm2 activity, whereby p53 function cannot be induced.

Ubiquitin-mediated proteolysis is an important pathway of non-lysosomal protein degradation that controls the timed destruction of a number of cellular regulatory proteins including p53. See Pagano, 1997 *FASEB J.* 11:1067. Ubiquitin is an evolutionary highly conserved 76-amino acid polypeptide which is abundantly present in eukaryotic cells. The ubiquitin pathway leads to the covalent attachment of poly-ubiquitin chains to target substrates which are then degraded by a multi-catalytic proteasome complex.

A number of the steps of regulating protein ubiquitination are known. In particular, initially the ubiquitin activating enzyme (E1) forms a high energy thioester linkage with ubiquitin. Ubiquitin is then transferred to a reactive cysteine residue of one of many ubiquitin conjugating enzymes known as Ubc or ubiquitin E2 enzymes. The final transfer of ubiquitin to a target protein involves one of many ubiquitin protein ligases (E3s). Mdm2 is such a ubiquitin ligase that mediates the transfer of ubiquitin to p53. See also WO05047476.

The human immunodeficiency virus (HIV) including HIV type 1 (HIV-1, also referred to as HTLV-III LAV or HTLV-III/LAV) and, to a lesser extent, human immunodeficiency virus type 2 (HIV-2) is the etiological agent of the acquired immune deficiency syndrome (AIDS) and related disorders. Barre-Sinoussi, et al., *Science,* 220:868-871 (1983).

Efforts to identify certain agents that can inhibit retroviral replication by modulating ubiquitination of a host cell protein has been reported. U.S. Patent Publication 2005/0112562.

It thus would be desirable to have new compounds that have use in treatment of undesired cell proliferation, including in treatment against cancer cells, as well as for treatment against viral infections, particularly to treat retroviral-infected mammalian cells. It would be especially desirable to have new compounds that could modulate or stabilize p53 activity by inhibiting Mdm2-mediated ubiquitination.

SUMMARY OF THE INVENTION

We have now found new pyrazolidinyl compounds and therapeutic uses of such compounds.

In one aspect, compounds of the invention are useful as anti-cancer agents.

In a further aspect, compounds of the invention are useful to a disorder or disease where inflammation or an immune response is exhibited.

In another aspect, compounds of the invention are useful in anti-viral therapies, including to treat against a retroviral infection in mammalian cells, particularly an HIV infection.

We have found that preferred pyrazolidinyl compounds can stabilize p53 and induce apoptosis in mammalian cells through selective inhibition of ubiquitin E1. Preferred pyrazolidinyl compounds additionally can inhibit Mdm2 autoubiquitination, in vitro cyclin E degradation, and/or TNF-induced TRAF6 ubiquitination, as well as TNF-induced phosphorylation and degradation of IκBα in cells. See for instance, the results set forth in the Examples, which follow.

In a particular aspect, the invention provides compounds of the following Formula (I), or pharmaceutically acceptable salt, solvate or hydrate thereof:

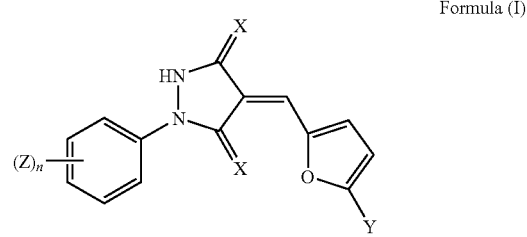

Formula (I)

wherein,
each X is independently O, S or NR$^1$;
each R$^1$ is independently H, alkyl, alkenyl, alkynyl, cycloalkyl, aralkyl, or heteroaralkyl, is C(O)R, C(O)OR, or C(O)NRR$^2$, each optionally substituted with a substituent;
each R$^2$ is independently H, alkyl, alkenyl, alkynyl, cycloalkyl, aralkyl, or heteroaralkyl, each optionally substituted with a substituent;

each R is independently H, alkyl, alkenyl, alkynyl, cycloalkyl, aralkyl, or heteroaralkyl, each optionally substituted with a substituent;

Y is H, alkyl, alkenyl, alkynyl, cycloalkyl, aralkyl, heteroaralkyl, aryl, heteroaryl, nitro, or halogen;

wherein the alkyl, alkenyl, alkynyl, cycloalkyl, aralkyl, heteroaralkyl, aryl, or heteroaryl groups may be substituted with H, halogen, nitro, cyano, alkoxy, thioalkoxy, $NR^3R^4$, $S(O)R^5$, $S(O)_2R^5$;

wherein each of $R^3$ and $R^4$ are independently selected from H, alkyl, aralkyl, or aryl;

wherein $R^5$ is OH, $OR^3$, $NH_2$, or $NHR^3$;

Z is H, alkyl, alkenyl, alkynyl, cycloalkyl, aralkyl, heteroaralkyl, aryl, heteroaryl, halogen, $C(O)R^3$, $C(O)OR^3$, $C(O)SR^3$, $C(O)NR^3R^4$, $C(S)OR^3$, $C(NR^1)OR^3$, $C(NR^1)NR^3R^4$; and n is an integer of zero to 5.

In another aspect, the invention provides compounds of the following Formula (II), or pharmaceutically acceptable salt, solvate or hydrate thereof:

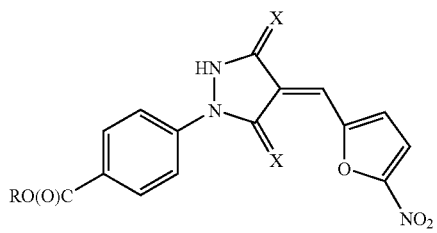

Formula (II)

wherein, each X is independently O, S or $NR^1$;

each $R^1$ is independently H, alkyl, alkenyl, alkynyl, cycloalkyl, aralkyl, or heteroaralkyl, is C(O)R, C(O)OR, or $C(O)NRR^2$, each optionally substituted with a substituent;

each $R^2$ is independently H, alkyl, alkenyl, alkynyl, cycloalkyl, aralkyl, or heteroaralkyl, each optionally substituted with a substituent;

each R is independently H, alkyl, alkenyl, alkynyl, cycloalkyl, aralkyl, or heteroaralkyl, each optionally substituted with a substituent.

The present invention further provides methods of treating or preventing an undesired cell proliferation disease or disorder such as cancer comprising the administration of a pyrazolidinyl compound to a patient susceptible to or suffering from an undesired cell proliferation disease or disorder such as cancer. Preferred methods of the invention are suitable for use in anti-cancer therapies and comprise the administration of one or more compounds of Formula I and/or Formula II, alone or in combination with other anti-cancer or anti-tumor therapeutics. Malignancies for treatment include both solid and disseminated cancers.

In a further aspect, the invention provides methods of treating or preventing a retroviral infection comprising the administration of a pyrazolidinyl compound to mammalian cells infected with or susceptible to infection by a retrovirus such as HIV. Such methods can include administering to a subject cells or a patient an effective amount of one or more pyrazolidinyl compounds particularly one or more compounds of Formula I and/or Formula II above. Preferably, such administration decreases or eliminates the pool of infected cells and/or decreases the viral population.

As discussed above, the invention also provides methods of treating or preventing a disease or disorder where inflammation or an immune response is exhibited comprising one or more pyrazolidinyl compounds (such as one or more compounds of Formulae I and/or II) to a subject. For instance, methods of the invention include treatment or prevention of a disease or disorder where inhibiting inflammation would have a beneficial effect, such as sepsis or severe sepsis, arthritis, inflammatory myocarditis, glomerulonephritis, inflammatory conditions of the gastrointestinal tract, such as inflammatory bowel disease, ulcerative colitis, and Crohn's Disease, inflammatory conditions of the central nervous system, asthma, lung fibrosis, glomerulonephritis, atherosclerosis, autoimmune encephalomyelitis, cystic fibrosis, rheumatoid arthritis, systemic inflammatory response syndrome and other NF-κB-mediated inflammatory disease states.

Indeed, it has been found that compounds of the invention (including compounds of Formulae I and II) are effective inhibitors of NFκB and can prevent activation of NFκB. See the examples which follow. See also Yang et al., *Cancer Research*, 67(19): 9472-9481 (2007).

It also believed that compounds of the invention (including compounds of Formulae I and II) can inhibit autophagy in mammalian cells, including primate cells such as human cells.

Therapeutic methods of the invention can also include the step of identifying that the subject is in need of treatment of diseases or disorders described herein, e.g., identifying that the subject is in need of treatment for cancer, or treatment for a disease or disorder where inflammation or an immune response is exhibited, or treatment for a retroviral infection. The identification can be in the judgment of a subject or a health professional and can be subjective (e.g., opinion) or objective (e.g., measurable by a test or a diagnostic method). Tests for cancer are known and may include e.g. analysis of patient sample (e.g. biopsed tissue, or patient fluid such as blood, saliva, etc.) and for cancer cells or protein markers of a cancer. Tests for retroviral infection such as HIV infection are known in the art and include polymerase chain reaction-based (PCR-based) amplification and detection of viral RNA; Western blot detection of anti-HIV antibodies; agglutination assays for anti-HIV antibodies; ELISA-based detection of HIV-specific antigens (e.g., p24); and line immunoassay (LIA). In each of these methods, a sample of biological material, such as blood, plasma, semen, or saliva, is obtained from the subject to be tested. Thus, the methods of the invention can include the step of obtaining a sample of biological material (such as a bodily fluid) from a subject; testing the sample to determine the presence or absence of detectable cancer of retroviral infection such as HIV infection, HIV particles, or HIV nucleic acids; and determining whether the subject is in need of treatment according to the invention.

The methods delineated herein can further include the step of assessing or identifying the effectiveness of the treatment or prevention regimen in the subject by assessing the presence, absence, increase, or decrease of a marker, including a marker or diagnostic measure of cancer or of a retroviral infection such as HIV infection, HIV replication, viral load, or expression of an HIV infection marker; preferably this assessment is made relative to a measurement made prior to beginning the therapy. Such assessment methodologies are known in the art and can be performed by commercial diagnostic or medical organizations, laboratories, clinics, hospitals and the like. As described above, the methods can further include the step of taking a sample from the subject and analyzing that sample. The sample can be a sampling of cells, genetic material, tissue, or fluid (e.g., blood, plasma, sputum, etc.) sample. The methods can further include the step of reporting the results of such analyzing to the subject or other health care professional. The method can further include additional steps wherein (such that) the subject is treated for the indicated disease or disease symptom.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, ape, monkey, or human), and more particularly a human. In one embodiment, the subject is an immunocompromised or immunosuppressed mammal, particularly a human (e.g., an HIV infected patient). In another embodiment, the subject is a mammal suffering from undesired cell growth, particularly a cancer, such as a human suffering from cancer.

The present invention further provides pharmaceutical compositions comprising one or more compounds according to Formulae I and/or Formula II, or salts thereof or solvate thereof, and preferably at least one pharmaceutically acceptable carrier.

The present invention also comprises methods of modulating Mdm2 autoubiquitination in a subject, which suitably comprise administering to the subject one or more compounds of Formulae I and/or II as set forth above in an amount and under conditions sufficient to modulate Mdm2 autoubiquitination. Preferably, the modulation is down-regulation. Effective dosage amounts and administration protocols can be readily determined empirically, e.g. by standard efficacy evaluations. Efficacy and thus Mdm2 autoubiquitination modulation can be assessed e.g. by therapeutic benefit as discussed herein, such as in vitro or in vivo treatment against cancer or viral infection.

The invention further comprises methods of modulating E1 to a greater extent than E2 or SUMO E1 in a subject, which suitably comprise administering to the subject one or more compounds of Formulae I and/or II as set forth above in an amount and under conditions sufficient to modulate E1 to a greater extent than E2 or SUMO E1. Effective dosage amounts and administration protocols can be readily determined empirically, e.g. by standard efficacy evaluations. Efficacy and thus modulation of E1 to a greater extent than E2 or SUMO E1 can be assessed e.g. by therapeutic benefit as discussed herein, such as in vitro or in vivo treatment against cancer or viral infection.

The invention also comprises methods of modulating E1 selectively in a subject, which suitably comprise administering to the subject one or more compounds of Formula I and/or II as set forth above in an amount and under conditions sufficient to modulate E1 selectively under conditions such that the E1 is altered selectively. Effective dosage amounts and administration protocols can be readily determined empirically, e.g. by standard efficacy evaluations. Efficacy and thus selective E1 modulation can be assessed e.g. by therapeutic benefit as discussed herein, such as in vitro or in vivo treatment against cancer or viral infection.

Compounds of the invention also will be useful to probe the function of the ubiquitin system and in inhibiting non-proteasomal functions of ubiquitination. In addition to its role in proteasomal degradation of target proteins, the ubiquitin system is also involved in a number of cellular processes unrelated to proteasomal degradation including endocytosis, trafficking in the endosomal system, viral budding, DNA repair, nucleocytoplasmic trafficking and kinase activation. Prior to the preferred present compounds, there have been limited tools that allow probing of the role of the ubiquitin system in these processes Other aspects of the invention are discussed invention.

BRIEF DESCRIPTION OF THE DRAWINGS

FIG. 1A depicts inhibition of autoubiquitination of GST-Mdm2 in vitro in the presence of various compounds identified through high throughput screening.

FIG. 1B depicts the inhibition of formation of E1-Ub complex in vitro by certain compounds. Labeled ubiquitin was used to examine the high-energy thiolester linkage between E1 and ubiquitin.

DETAILED DESCRIPTION OF THE INVENTION

Figure 2A:
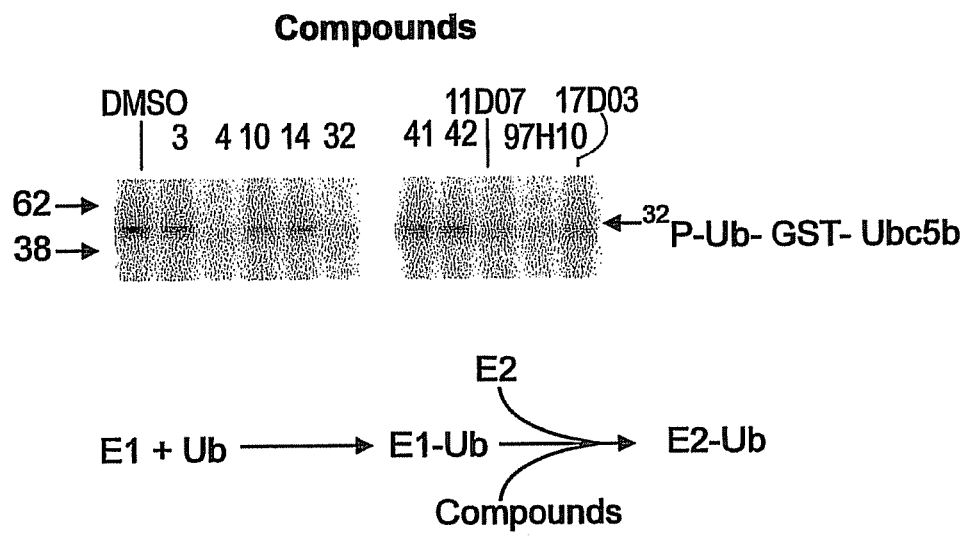
FIG. 2A depicts the inhibition of ubiquitin conjugation of E1 and E2 by some compounds, while others selectively inhibited only E2.

As discussed above, we now provide new pyrazolidinyl compounds and therapeutic uses of such compounds, including for use as anti-cancer and anti-viral agents.

Preferred pyrazolidinyl compounds can stabilize p53 and induce apoptosis in mammalian cells through selective inhibition of ubiquitin E1. Preferred pyrazolidinyl compounds additionally inhibit Mdm2 autoubiquitination, in vitro cyclin E degradation, and TNF-induced TRAF6 ubiquitination, as well as TNF-induced phosphorylation and degradation of IκBα in cells.

Therapeutic methods of invention include treating or preventing undesired cell growth, particularly cancer, tumors and the like. More preferably, the disease or disorder suitable for treatment by the methods of the invention include cancers selected from solid (tumors) and disseminated cancers particularly melanoma, carcinoma, leukemia, lymphoma, pediatric sarcoma, sarcoma, breast cancer, ovarian cancer, testicular cancer, prostate cancer, brain cancer, head or neck cancer, and lung cancer.

Therapeutic methods of the invention also include treating or preventing viral infections, particularly retroviral infections in mammalian cells, such as human cells infected with HIV.

Therapeutic methods of the invention further include treating or preventing a disease or disorder where inflammation or an immune response is exhibited, including NF-κB-mediated inflammatory disease states.

As discussed above, compounds of the following Formula (I), or pharmaceutically acceptable salt, solvate or hydrate thereof are provided as well as use of such compounds in the treatment of the diseases and disorders disclosed herein:

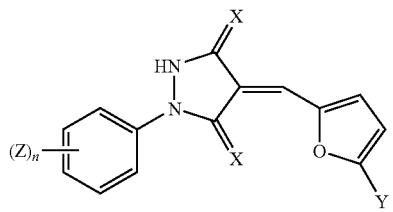

Formula (I)

wherein,
each X is independently O, S or $NR^1$;
each $R^1$ is independently H, alkyl, alkenyl, alkynyl, cycloalkyl, aralkyl, or heteroaralkyl, is C(O)R, C(O)OR, or $C(O)NRR^2$, each optionally substituted with a substituent;
each $R^2$ is independently H, alkyl, alkenyl, alkynyl, cycloalkyl, aralkyl, or heteroaralkyl, each optionally substituted with a substituent;
each R is independently H, alkyl, alkenyl, alkynyl, cycloalkyl, aralkyl, or heteroaralkyl, each optionally substituted with a substituent;
Y is H, alkyl, alkenyl, alkynyl, cycloalkyl, aralkyl, heteroaralkyl, aryl, heteroaryl, nitro, or halogen;
wherein the alkyl, alkenyl, alkynyl, cycloalkyl, aralkyl, heteroaralkyl, aryl, or heteroaryl groups may be substituted with H, halogen, nitro, cyano, alkoxy, thioalkoxy, $NR^3R^4$, $S(O)R^5$, $S(O)_2R^5$;
wherein each of $R^3$ and $R^4$ are independently selected from H, alkyl, aralkyl, or aryl;
wherein $R^5$ is OH, $OR^3$, $NH_2$, or $NHR^3$;
Z is H, alkyl, alkenyl, alkynyl, cycloalkyl, aralkyl, heteroaralkyl, aryl, heteroaryl, halogen, $C(O)R^3$, $C(O)OR^3$, $C(O)SR^3$, $C(O)NR^3R^4$, $C(S)OR^3$, $C(NR^1)OR^3$, $C(NR^1)NR^3R^4$; and
n is an integer of from 0 to 5.

In one embodiment, X is oxygen. In another embodiment, Y is H, nitro or aryl. In a further embodiment, the aryl group is phenyl. Preferably, the phenyl group is substituted with $S(O)_2R^5$, wherein $R^5$ is $NH_2$.

In another embodiment, Z is H, $C(O)OR^3$, or halogen. In a further embodiment, $R^3$ is alkyl. In another further embodiment, halogen is Br.

In one embodiment, n is 1. In another embodiment, Z is substituted at the para or ortho position.

In another aspect, compounds of the following Formula (II), or pharmaceutically acceptable salt, solvate or hydrate thereof are provided as well as use of such compounds in the treatment of the diseases and disorders disclosed herein:

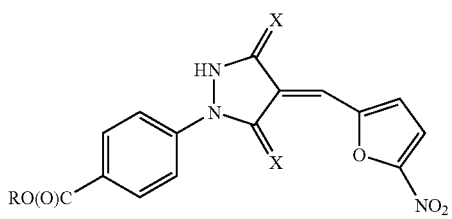

Formula (II)

wherein,
each X is independently O, S or $NR^1$;
each $R^1$ is independently H, alkyl, alkenyl, alkynyl, cycloalkyl, aralkyl, or heteroaralkyl, is C(O)R, C(O)OR, or $C(O)NRR^2$, each optionally substituted with a substituent;
each $R^2$ is independently H, alkyl, alkenyl, alkynyl, cycloalkyl, aralkyl, or heteroaralkyl, each optionally substituted with a substituent;
each R is independently H, alkyl, alkenyl, alkynyl, cycloalkyl, aralkyl, or heteroaralkyl, each optionally substituted with a substituent.

Specifically preferred compounds of the invention particularly for use in the therapeutic methods disclosed herein are the following (and salts and solvates thereof):

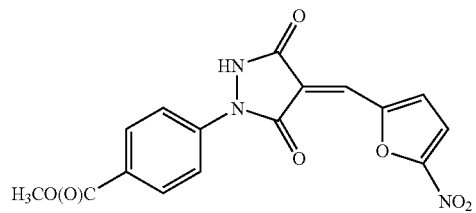

4-[4-(5-nitro-furan-2-ylmethylene)-3,5-dioxo-pyrazolidin-1-yl]-benzoic acid methyl acid;

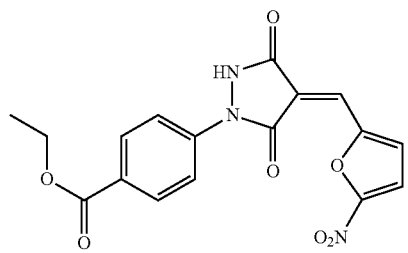

4-[4-(5-Nitro-furan-2-ylmethylene)-3,5-dioxo-pyrazolidin-1-yl]-benzoic acid ethyl ester;

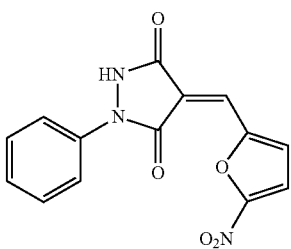

4-(5-Nitro-furan-2-ylmethylene)-1-phenyl-pyrazolidine-3,5-dione;

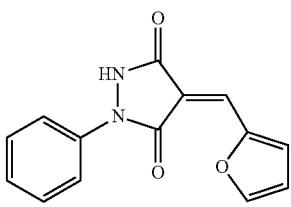

4-Furan-2-ylmethylene-1-phenyl-pyrazolidine-3,5-dione;

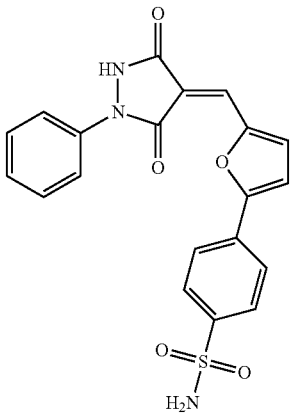

4-[5-(3,5-Dioxo-1-phenyl-pyrazolidin-4-ylidenemethyl)-furan-2-yl]-benzenesulfonamide;

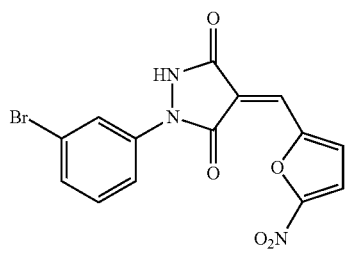

1-(3-Bromo-phenyl)-4-(5-nitro-furan-2-ylmethylene)-pyrazolidine-3,5-dione; and

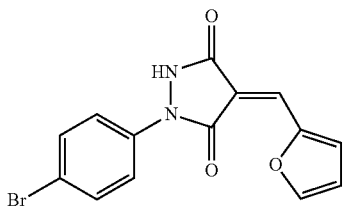

1-(4-Bromo-phenyl)-4-furan-2-ylmethylene-pyrazolidine-3,5-dione.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical. The term "ester" refers to a —C(O)O—R, where R is defined herein An "amido" is an —C(O)NH$_2$, and an "N-alkyl-substituted amido" is of the formula C(O)NHR, where R is defined herein. The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one non-aromatic. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclic" or similar term refers to a hydrocarbon 3-8 membered monocyclic or 7-14 membered bicyclic ring system having at least one non-aromatic ring, wherein the non-aromatic ring has some degree of unsaturation. Cyclic groups may be optionally substituted with one or more substituents. In one embodiment, 0, 1, 2, 3, or 4 atoms of each ring of a cyclic group may be substituted by a substituent. Examples of cyclyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a $(C_1-C_6)$alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl and the like.

As used herein, the term "alkylene" refers to an alkyl group that has two points of attachment. The term "$(C_1-C_6)$alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like.

The term "arylalkoxy" refers to an alkoxy substituted with aryl.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1-C_6)$alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents.

In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" or "hydroxylalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that do not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR$^c$).

In other embodiments, substituents on any group (such as, for example, alkyl, alkenyl, alkynyl, aryl, aralkyl, heteroaryl, heteroaralkyl, cycloalkyl, cyclyl, heterocycloalkyl, and heterocyclyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents an alkyl, alkenyl, alkynyl, aryl, aralkyl, heteroaryl, heteroaralkyl, cycloalkyl, cyclyl, heterocycloalkyl, and heterocyclyl include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (=O), (=S), (=NR$^{15}$), C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocyclyl, or heteroaryl. Each R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups.

Combinations of substituents and variables envisioned by this invention are preferably those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders or symptoms thereof). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of this invention include the compounds themselves, as well as their salts, solvate, hydrate, polymorph, or prodrugs, if applicable.

The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and ρ-toluenesulfonic acid.

The compounds herein are commercially available or can be synthesized. As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2nd. Ed., Wiley-VCH Publishers (1999); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

As discussed above, preferred pyrazolidinyl compounds are useful in cancer therapies. Preferred compounds of the formulae herein shows specificity in cells for inhibiting the E1 for ubiquitin relative to the ubiquitin-like modifier SUMO and does not inhibit E2 (UbcH5B). These preferred compounds inhibit ubiquitin-mediated degradation of substrates both in vitro and in cells, including the NFκB inhibitor (IκBα) and p53. They cause selective cell death of myeloma cells and of transformed p53-expressing fibroblasts that are predicted to be susceptible to apoptotic cell death in response to p53 reactivation. The compounds also activate a p53 response in cells. These E1 inhibitors are not only unique and valuable tools to probe the ubiquitination system, but also the basis for development of therapeutic agents that, among other things, can target NFκB to suppress inflammation, activate p53, and otherwise interfere with normal ubiquitin-mediated processes to kill tumor cells.

As discussed above, it has been found that pyrazolidinyl compounds of the present invention including those compounds represented by Formulae I and II above are capable of stabilizing p53. Although not being bound by any theory, it is believed that preferred compounds of the invention can stabilize p53 activity in transformed cells by inhibition of Mdm2. More particularly, it is believed compounds of the invention, including those compounds of Formulae I and II above, are capable of inhibiting the activity through inhibition of ubiquitin E1.

As discussed above, the invention includes methods for treating or preventing (prophylactic treatment) against undesired cell growth or proliferation.

Preferred therapeutic methods of the invention include treating malignancies, including solid tumors and disseminated cancers. Exemplary tumors that may be treated in accordance with the invention include e.g. cancers of the lung, prostate, breast, liver, colon, breast, kidney, pancreas, brain, skin including malignant melanoma and Kaposi's sarcoma, testes or ovaries, or leukemias or lymphomia including Hodgkin's disease.

As also discussed above, the invention includes methods for treating against a virus infection, including to treat mammalian cells that are infected with a retrovirus, particularly human cells that are infected with a retrovirus such as HIV.

As discussed above, the invention also provides methods of treating or preventing a disease or disorder where inflammation or an immune response is exhibited comprising one or more pyrazolidinyl compounds to a subject, including one or more compounds of Formulae I or II.

The therapeutic methods of the invention generally comprise administration of an effective amount of one or more compounds of the invention to cells or a subject including a mammal, such as a primate, especially a human, in need of such treatment. The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The treatment methods of the invention also will be useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention may be administered singularly (i.e., sole therapeutic agent of a regime) to treat or prevent diseases and conditions such as undesired cell proliferation and/or viral infection as disclosed herein.

Compounds of the invention also may be administered as a "cocktail" formulation, i.e., coordinated administration of one or more compounds of the invention together with one or more other active therapeutics.

For instance, for a chemotherapy application, one or more pyrazolidinyl compounds of the invention including those of Formulae I and II may be administered in coordination with a regime of one or more other chemotherapeutic agents, particularly a compound that functions against cancer cells other than by p53 stabilization such as an antineoplastic drug, e.g., an alkylating agent (e.g., merchloroethamine, chlorambucil, cyclophosphamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of the invention include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer.

A particularly suitable combination protocol may include coordinated administration of one or more compounds of the invention with a compound that can activate but not necessarily stabilize p53, e.g. a therapeutic agent that can enhance interaction of p53 with histone acetylases.

For an antiviral therapy, one or more pyrazolidinyl compounds of the invention including those of Formula I may be administered in coordination with a regime of one or more other antiviral agents such as reverse transcriptase inhibitors such as dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (GlaxoWellcome), atazanavir (Bristol Myers Squibb), amprenavir (GlaxoSmithKline), fosamprenavir (GlaxoSmithKline), tipranavir (Boehringer Ingleheim), KALETRA (lopinavir+ritonavir, Abbott), and other agents such as 9-(2-hydroxyethoxymethyl)guanine (acyclovir), interferon, e.g., alpha-interferon, interleukin II, and phosphonoformate (Foscarnet), or entry inhibitors, e.g., T20 (enfuvirtide, Roche/Trimeris) or UK-427,857 (Pfizer), or in conjunction with other immune modulation agents or treatments including bone marrow or lymphocyte transplants or other medications such as levamisol or thymosin which would increase lymphocyte numbers and/or function as is appropriate. Because many of these drugs are directed to different targets, e.g., viral integration, a synergistic may result with this combination.

In one embodiment, one or more compounds of the invention including those of the formulae herein are used in conjunction with one or more therapeutic agents useful for treatment or prevention of HIV, a symptom associated with HIV infection, or other disease or disease symptom such as a secondary infection or unusual tumor such as herpes, cytomegalovirus, Kaposi's sarcoma and Epstein-Barr virus-related lymphomas among others, that can result in HIV immunocompromised subjects.

In certain embodiments of the invention, one or more pyrazolidinyl compounds of the invention including those of Formulae I and II above are used in conjunction with a standard HIV antiviral treatment regimens. This combination is advantageous in that the compound(s) of the formulae herein can activate latent HIV infected cells to replicate by stimulating lytic viral replication, thus making them susceptible to the co-administered standard HIV antiviral treatment regimens. In this manner, the latent or secondary reservoirs of HIV-infected cells are depleted through "controlled" activation (rather then serendipitous or uncontrolled activation), resulting in more complete elimination of infection. In another aspect, the treatment methods herein include administration of a so-called HIV-drug "cocktail" or combination therapy, wherein a combination of reverse transcriptase inhibitor(s) and HIV protease inhibitor(s) is co-administered.

For antiviral therapies, in a particular aspect, pyrazolidinyl compounds of the invention can be administered to HIV infected individuals or to individuals at high risk for HIV infection, for example, those having sexual relations with an HIV infected partner, intravenous drug users, etc.

Compounds of the invention can be administered by a variety of routes, such as orally or by injection, e.g., intramuscular, intraperitoneal, subcutaneous or intravenous injection, or topically such as transdermally, vaginally and the like.

In a particular embodiment, the compounds of the invention are administered intravenously. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base additional salts may be prepared. Lists of additional suitable salts may be found, e.g., in *Remington's Pharmaceutical Sciences*, $17^{th}$ ed., Mack Publishing Company, Easton, Pa.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a compound of the invention packaged together with instructions (written) for therapeutic use of the compound, particularly to treat a subject suffering from or susceptible to cancer. Most preferred method of treating the patient with the pharmaceutical compositions of the invention, is administration of the compositions intravenously. However, other routes of administration of the pharmaceutical compositions can be used.

For oral administration, pharmaceutical compositions containing one or more compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampoules are convenient unit dosages.

The actual amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day; or any dosage range in which the low end of the range is any amount between 0.01 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day). The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage; or any dosage range in which the low end of the range is any amount between 0.05 mg/day and 400 mg/day and the upper end of the range is any amount between 1 mg/day and 500 mg/day (e.g., 5 mg/day and 100 mg/day, 150 mg/day and 500 mg/day).

A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

The invention also provides kits for treatment or prevention of a disease or disorder (or symptoms) thereof associated with ubiquitination. In one embodiment, the kit includes an effective amount of a compound herein in unit dosage form, together with instructions for administering the compound to a subject suffering from or susceptible to a disease or disorder or symptoms thereof associated with ubiquitination, wherein the effective amount of a compound is as described herein. In preferred embodiments, the kit comprises a sterile container which contains compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound for treatment of a disease or disorder or symptoms thereof associated with ubiquitination, including treatment of cell proliferative diseases and disorders, and/or treatment of a disease or disorder where inflammation or an immune response is exhibited and/or treatment of viral infections particularly retroviral infections such as HIV infections; in preferred embodiments, the instructions include at least one of the following: description of the compound; dosage schedule and administration for treatment of a disease or disorder or symptoms; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

As discussed above, the invention also provides methods (also referred to herein as "screening assays") for identifying candidate compounds useful for treatment against cancer cells or other undesired cell proliferation. Screening assays can be adapted to a high throughput format to enable the rapid screening of a large number of compounds. Assays and screening methods can be used for identification of compounds possessing E1-specific, Mdm2-specific and/or general inhibition of ubiquitin enzyme inhibitory activity. Thus, in accordance with the invention, methods are provided to screen candidate compounds which exhibit potential anticancer activity by measuring p53 stability in transformed cells and/or apoptosis and cell death.

The ubiquitin activating enzyme (E1) forms a high energy thioester linkage with ubiquitin. Ubiquitin is then transferred to a reactive cysteine residue of one of many ubiquitin conjugating enzymes known as Ubc or ubiquitin E2 enzymes. The final transfer of ubiquitin to a target protein involves one of many ubiquitin protein ligases (E3s). Mdm2 is such a ubiquitin ligase that mediates the transfer of ubiquitin to p53.

Mdm2 protein binds tumor suppressor p53 and targets it for ubiquitination and proteosome-mediated degradation. Mdm2 is a RING finger-containing E3 for p53. Mdm2 also catalyzes self-ubiquitination, and thus regulates intracellular levels of both p53 and itself. Without wishing to be bound by theory, molecules which inhibit the activity of ubiquitin E1, and thus inhibit Mdm2 activity, including the activity of Mdm2 with respect to p53 could be important in identifying potential drug compounds that affect p53 stability. Similarly, interference with the expression of E1 by a candidate drug compound can identify anti-tumor compounds that can be further analyzed using a high-throughput assay described below. As a theoretical illustrative example, expression may be down regulated by administering small molecules and peptides which specifically inhibit E1 expression can also be used.

In theory, such inhibitory molecules can be identified by screening for compounds which interfere with the formation of thiolester linkages between ubiquitin and E1 where one of the binding partners is bound to a solid support and the other partner is labeled. Antibodies specific for epitopes on ubiquitin or E1 which are involved in the binding interaction will interfere with such binding. Solid supports which may be used include any polymers which are known to bind proteins. The support may be in the form of a filter, column packing matrix or sephadex beads. Labeling of proteins can be accomplished according to many techniques. Radiolabels, enzymatic labels, and fluorescent labels can be used. Alternatively, both ubiquitin and E1 may be in solution and bound molecules separated from unbound subsequently. Any separation technique may be employed, including immunoprecipitation or immunoaffinity separation with an antibody specific for the unlabeled binding partner.

The ability of a compound to inhibit E1 activity may also be examined by determining the ability of the compound to inhibit Mdm2 autoubiquitination, which is dependent on E1, as well as E2. For in vitro assays Mdm2 can be expressed as a GST fusion. This allows for a high level of expression of protein that can be purified on glutathione Sepharose. Detection of ubiquitination of Mdm2 can be accomplished, for example, using $^{32}$P-labeled ubiquitin, Western blotting with anti-ubiquitin, or by looking at a shift in the molecular weight of GST fusion by Western blotting with anti-GST. A variety of in vitro assays that measure levels of self-ubiquitinated Mdm2 can be employed, such as for example, immunoprecipitation of ubiquitinated Mdm2; gel assays wherein the amount of ubiquitinated Mdm2 is measured by densitometric scanning or where covalent attachment of radio-labeled or otherwise tagged ubiquitin to Mdm2 or p53 is measured; Western blot analysis, or other known techniques such as ELISA, immunoprecipitation, RIA, and the like. Candidate compounds that inhibit self-ubiquitination of Mdm2, as described in detail in the Examples which follow, are detected by a shift in molecular weight either of Mdm2 or of ubiquitin that becomes covalently attached to Mdm2 (See for example Lorrick K L., et al., *Proc. Natl. Acad. Sci.* USA, 1999, 96:11364-11369; Fang S., et al., *J. Biol. Chem.*, 2000, 275 (12)8945-8951; Ryan K M., et al., *Curr. Op. Cell Biol.*, 2001, 13:332-337; which are herein incorporated by reference in their entirety). Mdm2 self-ubiquitination assays are run (see for example the results described in the Examples section) in the presence or absence of a known amount of candidate compound. An aliquot of each of the test and control reactions are run on a standard SDS-PAGE gel. Test reactions whereby the candidate compounds inhibit the self-ubiquitination of Mdm2 will have a decrease in high molecular weight ubiquitinated Mdm2.

In cellular assays, endogenous or transfected Mdm2 is used. For transfected Mdm2, ubiquitination is evaluated by an upward smear by anti-Mdm2 Western blotting after resolution of cell lysates on SDS-PAGE. Alternatively, immunoprecipitation can be accomplished by subjecting lysates from cells (treated and untreated cells) to anti-Mdm2, followed by Western Blotting and detecting ubiquitination by using anti-ubiquitin antibodies. Preferred screening methods comprise identifying a candidate compound based on assessment of p53 stabilization (e.g. half life of p53) and steady state levels, and the level of Mdm2, as compared to a control, e.g. normal (non-cancer cells).

Steady-state levels of p53 and Mdm2 in the cells can be determined by a number of approaches. For instance, lysates containing cellular protein can be immunoprecipitated with, for example, a rabbit anti-p53 polyclonal antibody or Mdm2 polyclonal antibody, blotted onto polyvinylidenedifluoride (PVDF) membranes and probed with a monoclonal antibody cocktail comprising, for example, monoclonal antibodies to various epitopes of p53, or Mdm2. Such antibodies are commercially available. Immunoblot analyses of cellular extracts, taken at different time points after treatment with a candidate compound is determinative of the half-life of p53 as compared to normal controls. Thus, increase or decrease in levels of p53 over periods of time is determinative of p53 stability based on its half-life and steady state levels. The lysates can be further purified, for example, by immunoprecipitation of p53 and/or Mdm2 directly or indirectly of Mdm2 and p53, or by affinity chromatography. Thus, candidate compounds that inhibit Mdm2 ubiquitin ligase activity, can be screened for any effect on p53 stability.

Cell-based assays include model systems where primary human epithelial cells ("normal cells") are compared to the same cells expressing the adenovirus E1A oncogene ("transformed cells"). Activation of p53 was not toxic to normal cells, but activation of p53 in transformed cells induces p53-mediated apoptosis. High concentrations of wild type (wt) p53 protein can induce apoptosis in a variety of different tumor cells. Potential inhibitors of Mdm2 would regulate the stability and function of p53 and Mdm2 Preferably the assays measure number of cells undergoing apoptosis due to Mdm2 induced p53 degradation in tumor cells in the presence or absence of candidate compounds as compared to normal cells in the presence or absence of candidate compounds. An increase in the number of these cells undergoing apoptosis in the presence of candidate compounds in tumor cells, as compared to normal untreated cells is indicative of a potential anti-tumor compound. Preferably a candidate compound increases apoptosis of tumor cells by at least 20% as compared to a control (no candidate compound administered), more preferably a candidate compound increases apoptosis of a tumor cell by at least about 30%, 40%, 50%, 60%, 70%, 80%, 90% or 100% as compared to a control (no candidate compound administered). That is, for example 80% increase of apoptosis refers to a decrease in the numbers of cells still surviving as compared to the controls.

Apoptosis can be measured by a variety of techniques. For example, apoptosis can be measured by determination of cell phenotype. Phenotype refers to how the cell looks, typically microscopically, but gross or macroscopic appearance can be observed. The phenotype changes depending on the growth rate of the cells. For instance, the microscopic morphology of cells that are rapidly dividing and growing is different than that of cells undergoing cell death by apoptosis. Determination of cell phenotype is well within the ability of one of ordinary skill in the art.

There are also a number of biochemical assays that can be used to detect apoptosis, such as "laddering" of the cellular DNA. When testing compounds for the ability to induce apoptosis, cell death (not cytostasis) is an endpoint of a compound application to the cell. A classic signature of apoptosis is the cleavage of nuclear DNA into nucleosomal subunits. On gels, this gives rise to the appearance of a ladder as nucleosomal units are sequentially cleaved from DNA. Observation of a classic DNA ladder is indicative of apoptosis. For example, cells are lysed and the high molecular weight DNA is removed by centrifugation. The aqueous phase is treated with proteinase K to digest proteins. After a phenol/chloroform extraction, the pellet is dissolved in deionized water and treated with 500 µg/ml RNaseA. The DNA is run on a 2% agarose minigel. Observation for a classic DNA ladder is made and a photograph can be taken. Cell death is verified by the demonstration of DNA as represented by the ladder configurations on the gel (see for example, White E., et al. 1984, *J. Virol.* 52:410). There are also a variety of other assays available for apoptosis such as "TUNEL" assays (see Gavrieli, Y., et al. (1992) *J. Cell. Biol.* 119:493).

As discussed above, the invention assays and screening methods for identification of other compounds possessing anti-cancer activity, including Mdm2-specific and/or general inhibition of ubiquitin enzyme inhibitory activity. Thus, in accordance with the invention, methods are provided to screen candidate compounds which exhibit potential anti-cancer activity by measuring p53 stability in transformed cells and/or apoptosis and cell death.

We also have found that compounds of the invention are not readily removed (e.g. washed away by buffer solutions) once added to E1. Additionally, we have found that biological activity of compounds of the invention as disclosed herein can be substantially inhibited or prevented by treatment with an excess of reduced glutathione. This indicates that the compounds can act as a nucleophile for the active site thiol of E1 (e.g., a central double bond of a compound can serve as Michael-acceptor for the nucleophilic thiol in a Michael-type reaction).

We have further found that compounds of the invention can prevent or inhibit activation of Nfkb. In particular, such inhibition of Nfkb activation has been shown in cell-based reporter assay.

This invention is further illustrated by the following examples which should not be construed as limiting. The contents of all references, patents and published patent applications cited throughout this application, as well as the figures, are incorporated herein by reference.

Example 1

Evaluation of Small Molecules that Inhibit Mdm2 Autoubiquitination

Fifty-two compounds that significantly inhibited autoubiquination of GST-Mdm2 were selected for further evaluation in the laboratory using a gel-based ubiquitination assay utilizing $^{32}$P-labeled ubiquitin. Most of these compounds inhibited Mdm2 autoubiquitinzation (some examples are shown in FIG. 1A). Since Mdm2 autoubiquitination depends on the activity of E1 and E2, some of these might act by inhibiting E1. In fact, some did block the formation of thio-lester linkages between $^{32}$P-labeled ubiquitin and E1 (FIG. 1B). The compound 4-[4-(5-nitro-furan-2-ylmethylene)-3,5-dioxo-pyrazolidin-1-yl]-benzoic acid methyl acid was active at a concentration of 20-50 µM.

Figure 2B:
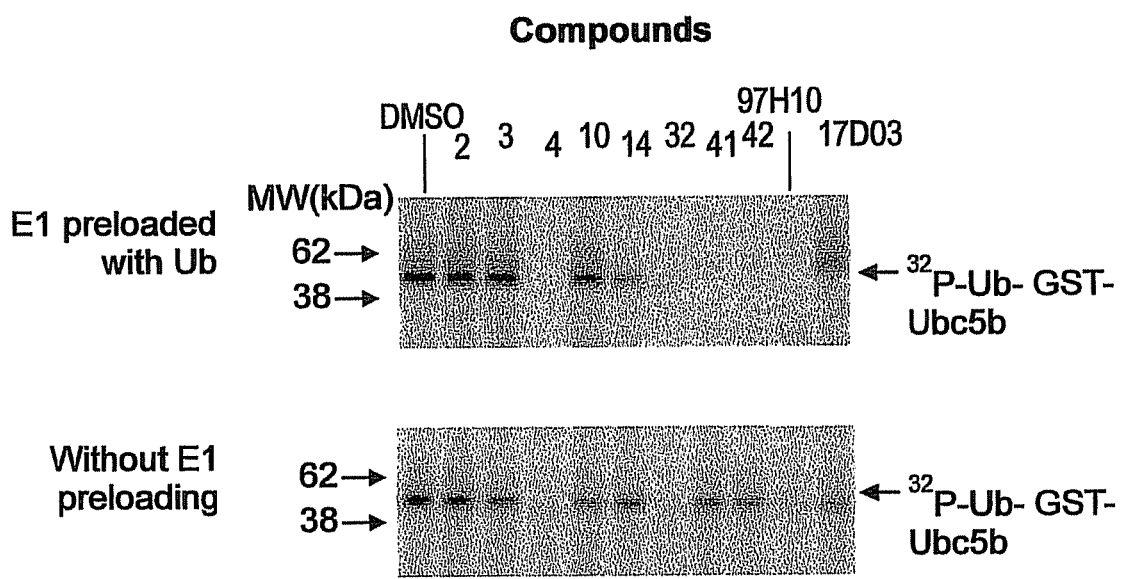
FIG. 2B depicts the effective prevention of E2-Ub conjugate formation by E1-selective inhibitors without preloading E1 with ubiquitin.

One way that the compounds might inactivate E1 is by alkylating or otherwise irreversibly inactivating active site cysteines. Like E1, E2 also uses a cysteine to form thiolester bond with ubiquitin. Inhibitors that directly act on the cysteine of E1 might therefore also affect E2 activity, and thus function in a relatively non-specific manner. To evaluate the effect of compounds on E2, we first loaded E1 with $^{32}$P-labeled ubiquitin, and then added E2 with the compounds to examine whether formation of E2-ubiquitin complex is prevented. As shown in FIG. 2A, several compounds identified in the screen effectively inhibited formation of E2-ubiquitin complex. However, the compound 4-[4-(5-nitro-furan-2-ylmethylene)-3,5-dioxo-pyrazolidin-1-yl]-benzoic acid methyl acid and the compound designated as "compound 41" did not affect transfer of ubiquitin from E1 to E2, indicating that these compounds do not function to non-specifically inhibit thiols. These findings are reinforced in FIG. 2B, where E2 thiolester formation is inhibited by the compound 4-[4-(5-nitro-furan-2-ylmethylene)-3,5-dioxo-pyrazolidin-1-yl]-benzoic acid methyl acid and compound 42 if the E1 is exposed to these compounds before loading with ubiquitin (lower panel), but not when the E1 is preloaded with ubiquitin (upper panel).

Figure 2C:
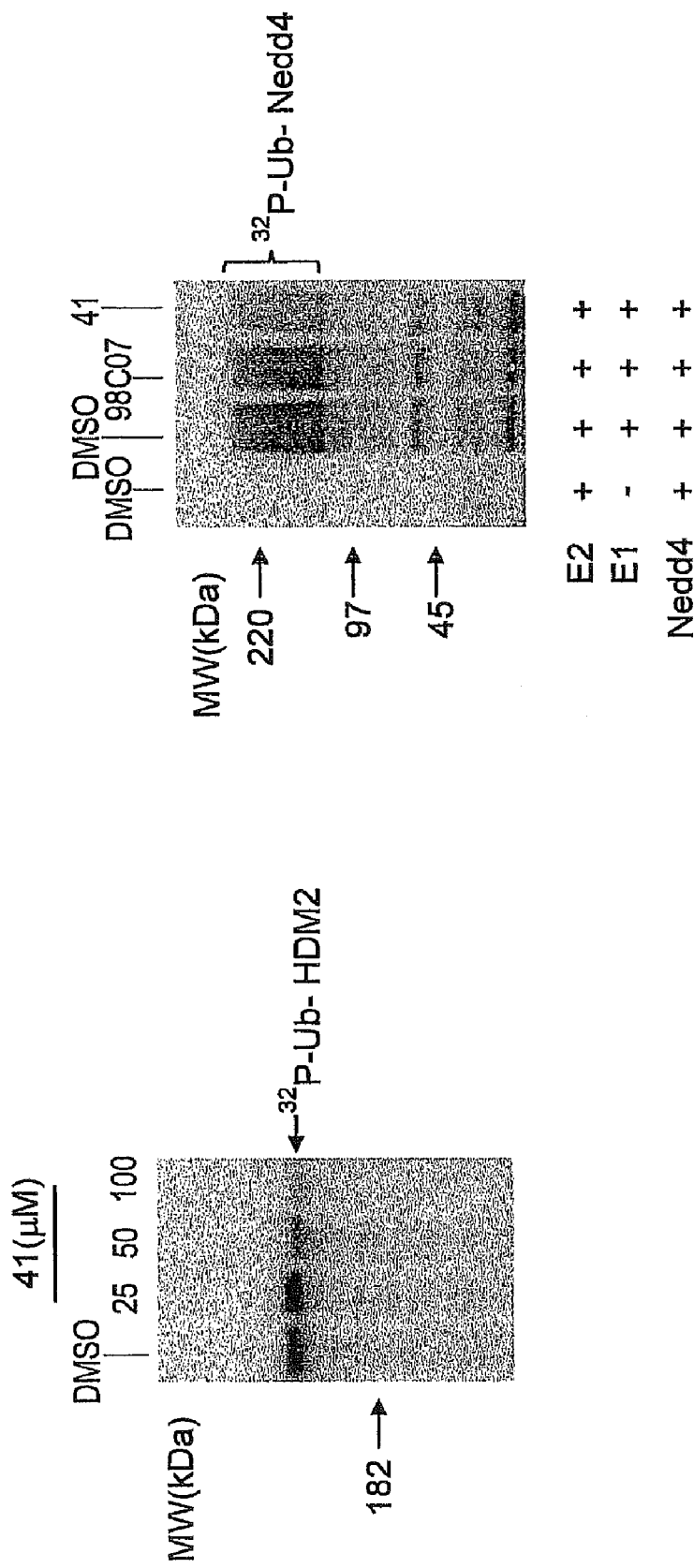
FIG. 2C depicts the inhibition of in vitro autoubiquitination of the RING finger E3 Mdm2 and the HECT domain E3 Nedd4.

It was then evaluated whether 4-[4-(5-nitro-furan-2-ylmethylene)-3,5-dioxo-pyrazolidin-1-yl]-benzoic acid methyl acid blocks autoubiquitination of both RING finger E3s (Mdm2) and HECT E3s (Nedd4) in vitro. As shown in FIG. 2C (left panel), 4-[4-(5-nitro-furan-2-ylmethylene)-3,5-dioxo-pyrazolidin-1-yl]-benzoic acid methyl acid can prevent generation of high molecular weight species promoted by Mdm2 in a dose-dependent manner. As predicted, the compound also inhibits the autoubiquitination of Nedd4 (right panel), whereas the Mdm2 inhibitor 98CO7 (10-(-3-chlorophenyl)-7-nitro-10H-pyrimido[4,5-b]quinoline-2,4-dione) only has very moderate effects. These results are consistent with an effect at the level of E1.

Example 2

E1 Inhibitor Inactivates E1 and Blocks Cyclin E Degradation In Vitro

Figure 3:
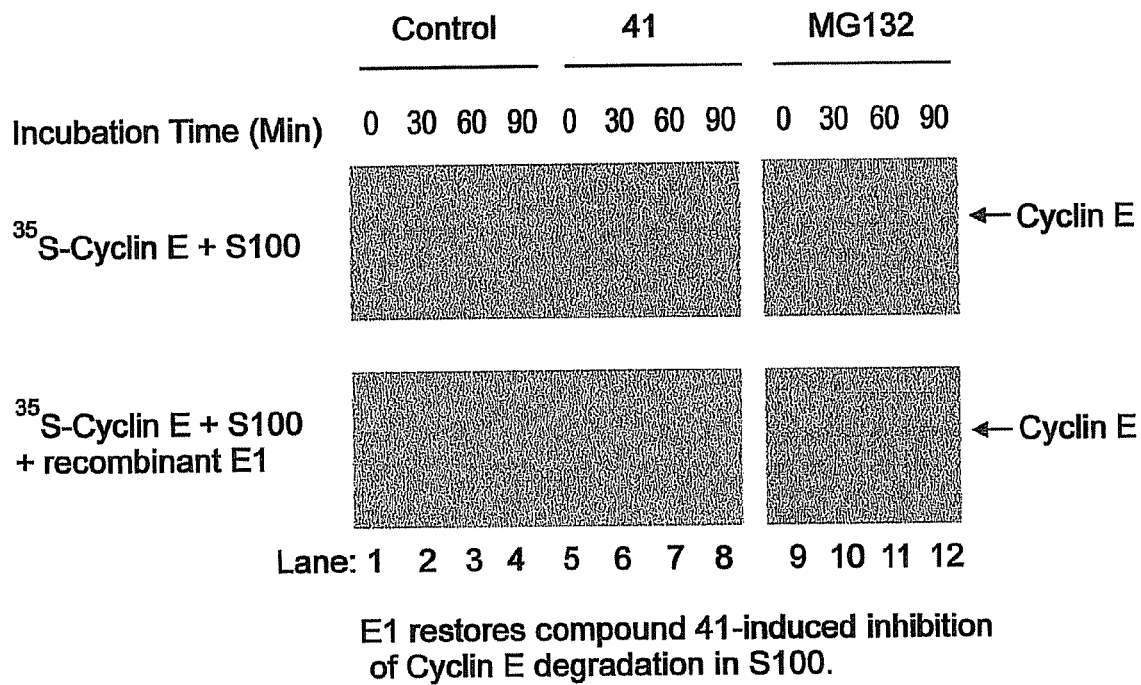
FIG. 3 depicts the restoration of 4-[4-(5-nitro-furan-2-ylmethylene)-3,5-dioxo-pyrazolidin-1-yl]-benzoic acid methyl acid-induced inhibition of cyclin E degradation in S100 by E1.

Cytosolic extracts from cells (S-100) contain all the components for ubiquitination and proteasomal degradation. To further evaluate 4-[4-(5-nitro-furan-2-ylmethylene)-3,5-dioxo-pyrazolidin-1-yl]-benzoic acid methyl acid, we made use of in vitro translated cyclin E, which is degraded in S-100 in a time-dependent manner (FIG. 3, upper panel, lanes 1-4). Both 4-[4-(5-nitro-furan-2-ylmethylene)-3,5-dioxo-pyrazolidin-1-yl]-benzoic acid methyl acid and the proteasome inhibitor MG132 block cyclin E degradation (FIG. 3, upper panel, lanes 5-12). However, when purified exogenous E1 is added to the reaction mixture, 4-[4-(5-nitro-furan-2-ylmethylene)-3,5-dioxo-pyrazolidin-1-yl]-benzoic acid methyl acid-mediated inhibition of cyclin E degradation was prevented (FIG. 3, lower panel, lanes 5-8). In contrast, when the block in degradation is distal to ubiquitination, as is the case with proteasome inhibition, addition of exogenous E1 is unable to overcome the block in cyclin E degradation (FIG. 3, lower panel, lanes 9-12).

Example 3

E1 Inhibitor Prevents TNF-Induced Degradation of IκBα

In order to evaluate 4-[4-(5-nitro-furan-2-ylmethylene)-3,5-dioxo-pyrazolidin-1-yl]-benzoic acid methyl acid in a cell-based system, the NFκB pathway was examined. NFκB is a critical transcription factor that controls expression of various genes involved in inflammation and immunity. In response to pro-inflammatory signals, the NFκB inhibitor IκBα is rapidly phosphorylated by IκB kinase (IKK), which leads to IκBα ubiquitination and its proteasomal degradation. Degradation of IκB allows NFκB to enter the nucleus and thereby regulate gene transcription. Ubiquitination has also more recently been shown to play important roles in IKK activation. IKK is activated by TRAF6, which must first be ubiquitinated with a K63-linked polyubiquitin chain.

Figure 4A:
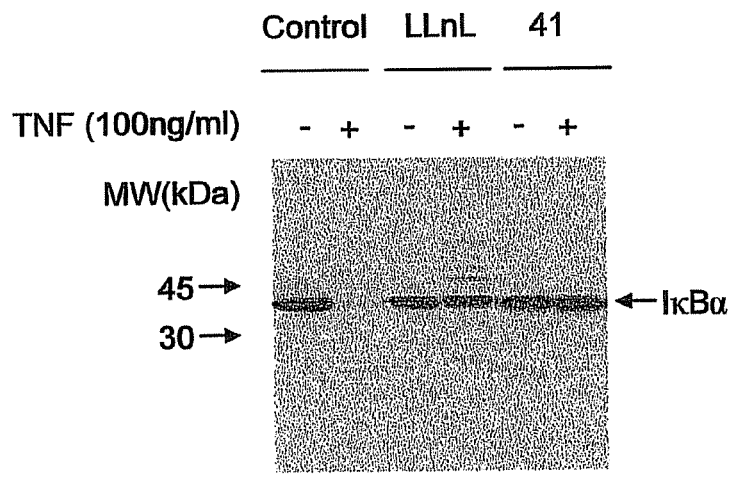
FIG. 4A depicts the inhibition of TNF-induced IκBα degradation by 4-[4-(5-nitro-furan-2-ylmethylene)-3,5-dioxo-pyrazolidin-1-yl]-benzoic acid methyl acid.
Figure 4B:
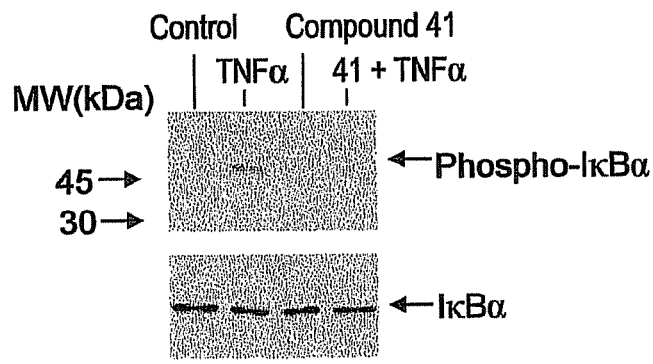
FIG. 4B depicts the inhibition of TNF-induced IκBα phosphorylation by 4-[4-(5-nitro-furan-2-ylmethylene)-3,5-dioxo-pyrazolidin-1-yl]-benzoic acid methyl acid.
Figure 4C:
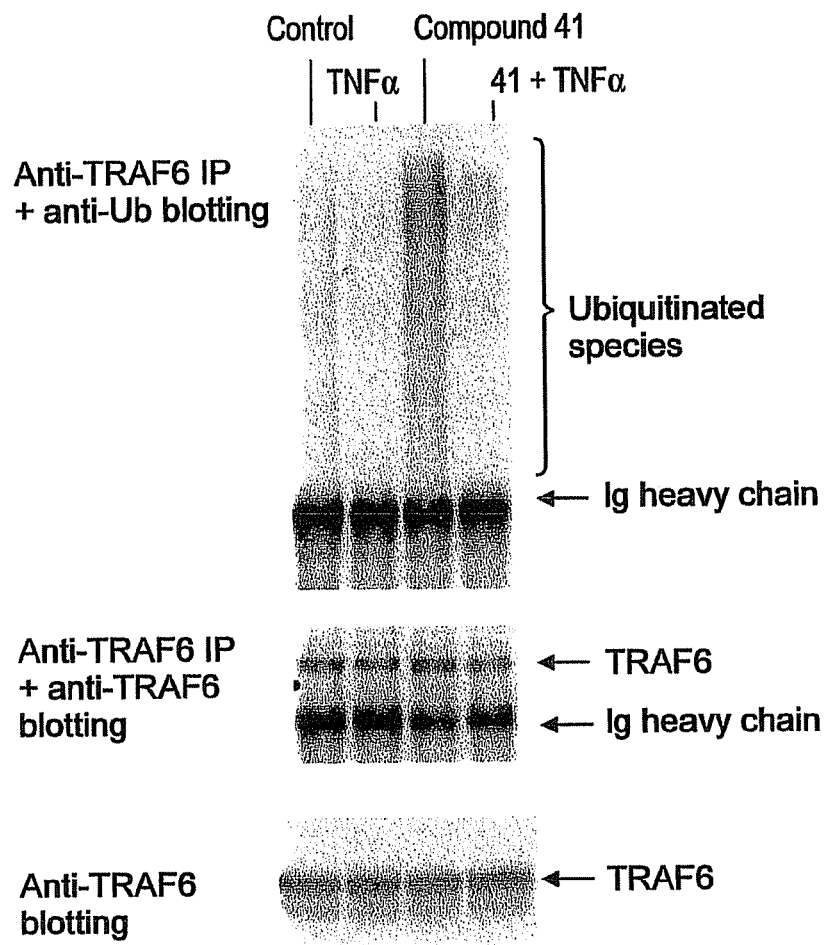
FIG. 4C depicts the inhibition of TNF-induced TRAF6 ubiquitination by 4-[4-(5-nitro-furan-2-ylmethylene)-3,5-dioxo-pyrazolidin-1-yl]-benzoic acid methyl acid.

As with the proteasome inhibitor ALLN, 4-[4-(5-nitro-furan-2-ylmethylene)-3,5-dioxo-pyrazolidin-1-yl]-benzoic acid methyl acid prevents TNFα-induced IκBα degradation (FIG. 4A). Moreover, 4-[4-(5-nitro-furan-2-ylmethylene)-3, 5-dioxo-pyrazolidin-1-yl]-benzoic acid methyl acid also blocks IκBα phosphorylation following TNFα treatment (FIG. 4B—1 minute stimulation), indicating that the compound acts upstream of IKK. To determine whether 4-[4-(5-nitro-furan-2-ylmethylene)-3,5-dioxo-pyrazolidin-1-yl]-benzoic acid methyl acid blocks ubiquitination of TRAF6 in response to TNFα, TRAF6 was immunoprecipitated from the T cell leukemia Jurkat after TNFα treatment, followed by immunoblotting (FIG. 4C). TNFα induced ubiquitination of TRAF, which was effectively inhibited by 4-[4-(5-nitro-furan-2-ylmethylene)-3,5-dioxo-pyrazolidin-1-yl]-benzoic acid methyl acid.

Example 4

Figure 5A:
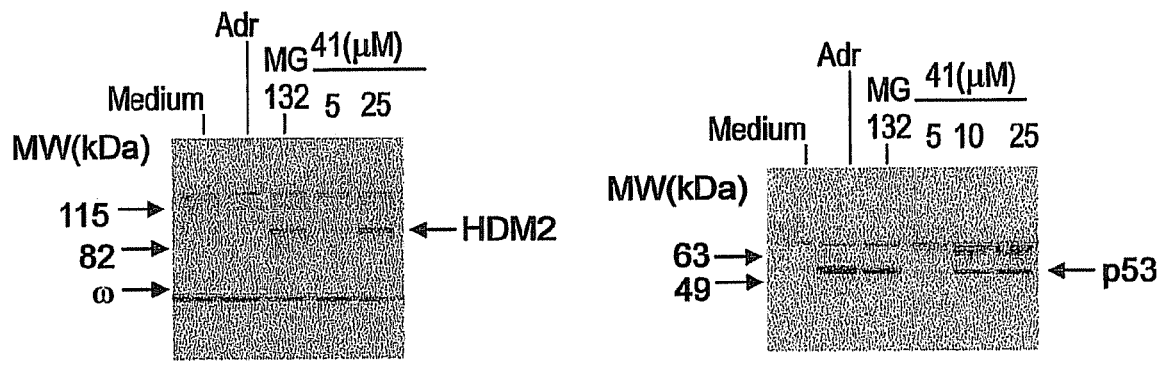
FIG. 5A depicts the increase in the levels of Mdm2 and p53 in RPE cells after treatment with the E1 inhibitor 4-[4-(5-nitro-furan-2-ylmethylene)-3,5-dioxo-pyrazolidin-1-yl]-benzoic acid methyl acid.
Figure 5B:
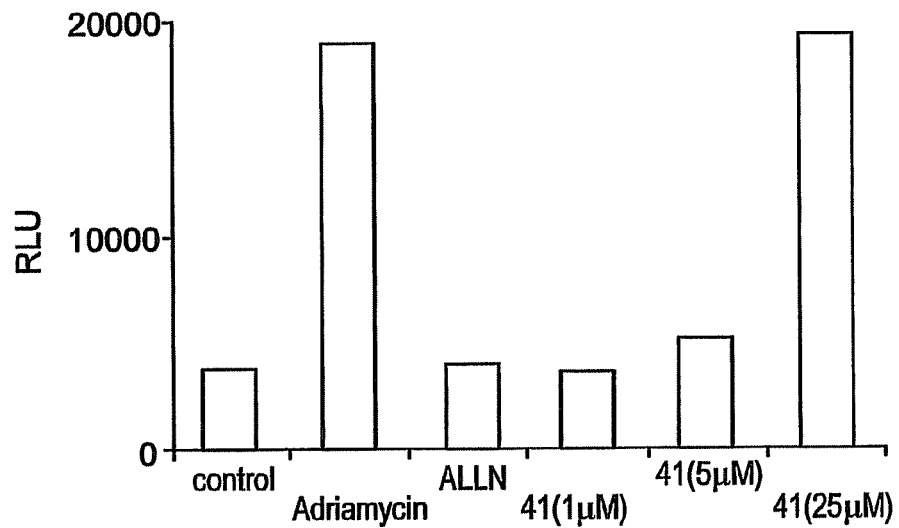
FIG. 5B depicts the results of reporter assays showing that the p53 induced by 4-[4-(5-nitro-furan-2-ylmethylene)-3,5-dioxo-pyrazolidin-1-yl]-benzoic acid methyl acid is transcriptionally active.

E1 Inhibitor Prevents P53 Degradation and Induces Apoptosis in Transformed Cells Since compound 41 inhibits autoubiquitination of Mdm2 in vitro, we next asked whether it increases cellular Mdm2 and p53. Immunoblotting revealed that, after six hours treatment, both Mdm2 and p53 are increased in cells (FIG. 5A). The p53 was found to be transcriptionally active, as it activated a p53-driven luciferase reporter to a level comparable to adriamycin (FIG. 5B).

Figure 6A:
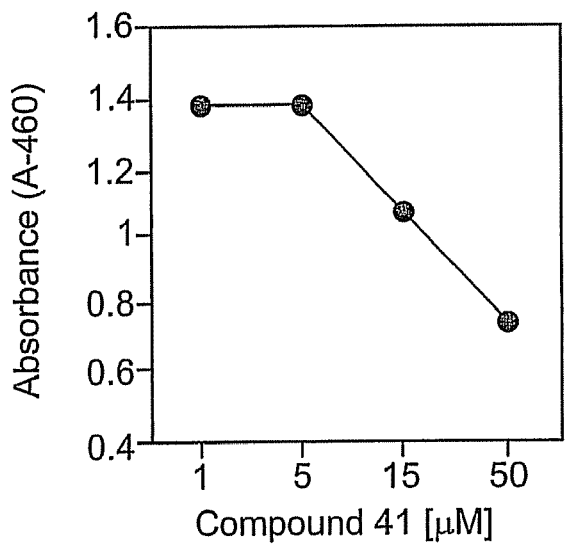
FIG. 6A depicts the induction of growth arrest in untransformed RPE cells by 4-[4-(5-nitro-furan-2-ylmethylene)-3,5-dioxo-pyrazolidin-1-yl]-benzoic acid methyl acid, as measured by MTT assay.
Figure 6B:
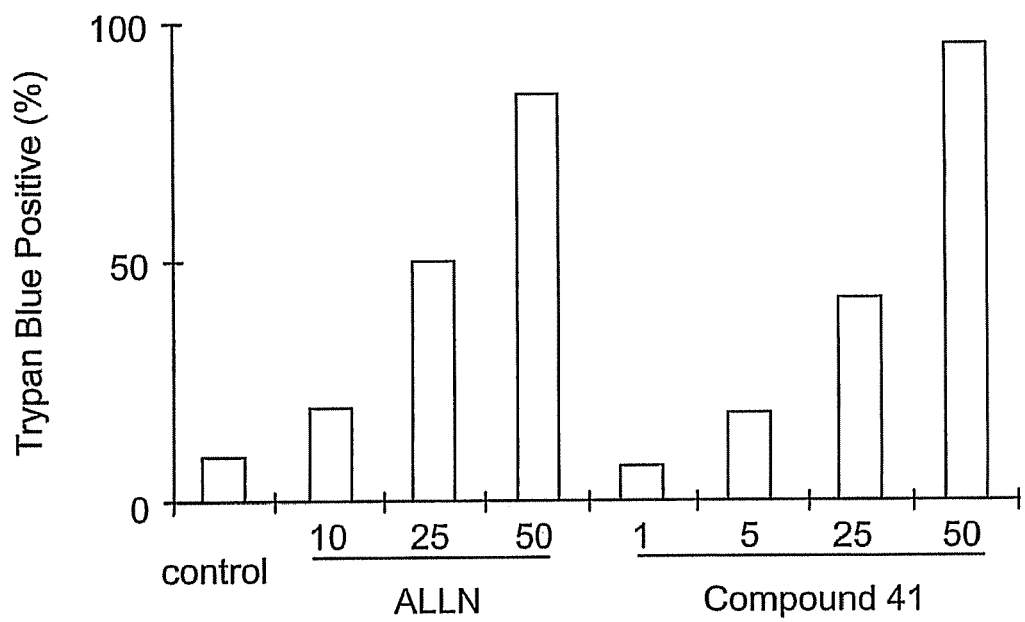
FIG. 6B depicts the dose-depending killing of J588 mouse myeloma cells by proteasome and E1 inhibitor by 4-[4-(5-nitro-furan-2-ylmethylene)-3,5-dioxo-pyrazolidin-1-yl]-benzoic acid methyl acid.

While p53 induces apoptotic cell death in many tumor cells, it generally only induces growth arrest in untransformed cells. This has been the rationale for many studies targeting the p53 system. We found that the E1 inhibitor causes growth arrest in untransformed retinal pigment epithelial cells (FIG. 6A), but strikingly kills myeloma cells in a dose-dependent manner (FIG. 6B). Furthermore, it only kills MEFs (mouse embryonic fibroblasts) that express wild type p53, whereas MEFs from p53-deficient mice are relatively resistant, indicating the cytotoxic action of inhibitor 4-[4-(5-nitro-furan-2-ylmethylene)-3,5-dioxo-pyrazolidin-1-yl]-benzoic acid methyl acid in these transformed cells is p53 dependent.

Example 5

E1 Inhibitor Prevents Loading of E1 with Ubiquitin in Cells

Figure 7A:
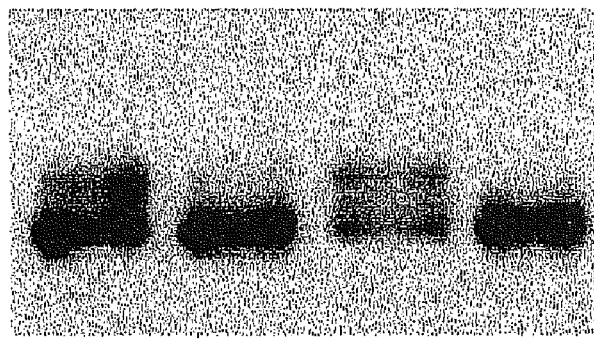
FIGS. 7A and 7B show that the E1 inhibitor 4-[4-(5-nitro-furan-2-ylmethylene)-3,5-dioxo-pyrazolidin-1-yl]-benzoic acid methyl acid can prevent or inhibit loading of E1 with ubiquitin in cells.
Figure 7B:
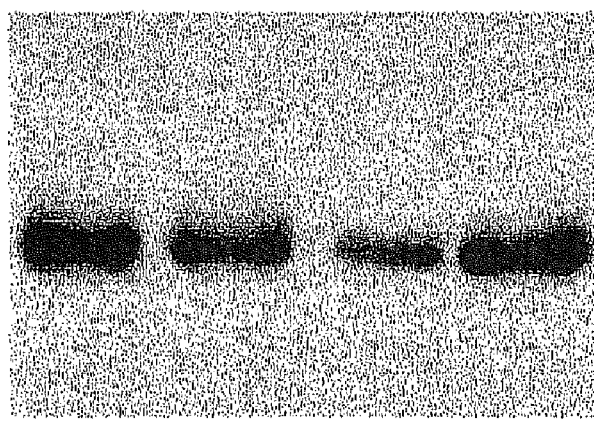

RPE cells were treated with the E1 inhibitor of 4-[4-(5-nitro-furan-2-ylmethylene)-3,5-dioxo-pyrazolidin-1-yl]-benzoic acid methyl acid (designated as EI-41, 50 µM), HLI98C (50 µM) or iodoacetamide 10 nM for 1 hour followed by lysis, SDS-PAGE under either non-reducing (FIG. 7A) or reducing (FIG. 7B) conditions and immunoblotting with anti-E1. Results are shown in FIGS. 7A and 7B, where the EI-41 compound is shown to inhibit the loading of EI with ubiquitin. Thus, as shown by the data in those figures, the EI-41 compound can inhibit E1-Ub thiol-ester formation in RPE cells.

Example 6

Figure 8:
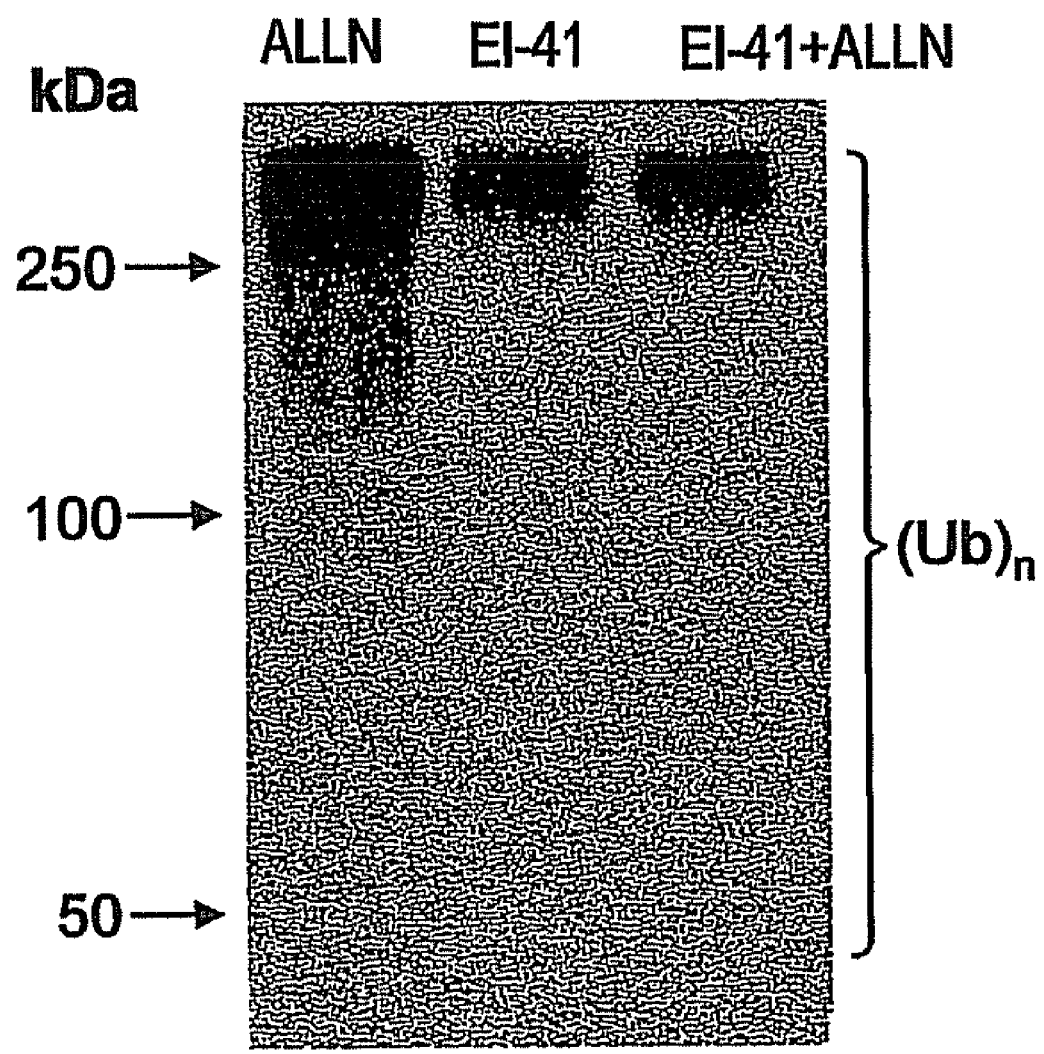
FIG. 8 shows that the E1 inhibitor 4-[4-(5-nitro-furan-2-ylmethylene)-3,5-dioxo-pyrazolidin-1-yl]-benzoic acid methyl acid can inhibit proteasome inhibitor-induced accumulation of ubiquitylated proteins.

E1 Inhibitor Inhibits Proteasome Inhibito-Induced Accumulation of Ubitquitylated Proteins U2O cells were treated with the E1 inhibitor of 4-[4-(5-nitro-furan-2-ylmethyl ene)-3,5-dioxo-pyrazolidin-1-yl]-benzoic acid methyl acid (designated as E1-41, 50 µM) and proteasome inhibitor (ALLN 50 µM) as indicated for four hours followed by lysis, SDS-PAGE under either non-reducing or reducing conditions and immunoblotting with anti-E1. Results are shown in FIG. 8, where the EI-41 compound is shown to inhibit the accumulation of ubiquiylated proteins in the proteasome inhibitor-treated cells.

Example 7

In Vitro Assays for Ubiquitination and Thiol-Ester Bond Formation

The following in vitro assays were employed as disclosed herein.

a. "Standard Mdm2 In Vitro Ubiquitination Assay" (E1+E2+E3 Assay)

5 pmole per experimental point of bacterially expressed GST-Mdm2 (or GST-Nedd) is coupled to glutathione Sepharose (GS) for 30 minutes at room temperature with tumbling, followed by 3× wash with 50 mM Tris pH 7.5. Following this, 20 µl of 1× buffer is added (40 µl 10× reaction buffer*, 40 µl 10× PCK**, 320 µl dH$_2$O). The test compound in DMSO is then added to the desired concentration with an equal volume of DMSO used as a control. Samples are incubated with shaking for 1 hr at 23° C. To carry out the reaction, a pre-made cocktail of Rabbit E1 (Calbiochem #6620700)/UbCH5B/$^{32}$P Ub cocktail (1 µl/0.5 µl/1 µl) is added followed by 15 minutes shaking at 30° C. The reaction is terminated by addition of 8 µl 4× reducing SDS-PAGE loading buffer. After dissociating proteins from the beads at 100° C. for 2 minutes, samples are resolved on 6% PAGE followed by exposure of the dried gel to phosphor screen. Note: $^{32}$P Ub is derived from GST-Ub that has been engineered to include a PKA phosphorylation site. This fusion protein is purified on glutathione Sepharose, phosphorylated, following this, the $^{32}$P Ub ubiquitin is cleaved and purified away from the thrombin.

*10× Buffer
500 mM Tris (pH 7.5)
2 mM ATP
5 mM MgCl$_2$
1 mM DTT
10 mM creatine phosphate (Sigma P4635) (45 mg/10 ml).
**10× PCK
Sigma C7886, 1000 U, reconstitute in 200 µl 10 mM Tris pH 8.0.

b. "E1 Only" Assay.

2 µl rabbit E1+12 µl of 1× reaction buffer are mixed together with the test compound followed by addition of 1 µl of $^{32}$P Ub. After incubating for 10 minutes at room temperature, the samples are denatured using loading buffer without reducing agent and subjected to SDS-PAGE under non-reducing conditions to maintain thiol-ester linkages and exposure as above.

c. E1+E2 Assay with Immobilized E2

20 pmoles of bacterially-expressed GST-UbcH5B are bound to GS beads for 30 minutes at room temperature. After washing in 50 mM Tris, pH 7.5, the test compounds were incubated with the beads in 20 µl of 1× reaction buffer at 23° C. for 1 hour. Rabbit E1/32P Ub cocktail (1 µl/1 µl) was then added to the mixture to incubate for another 60 minutes with shaking at 23° C. This is followed by resolution by SDS-PAGE under non-reducing conditions and exposure as above.

d. In Vitro P53 Ubiquitination Assay p53 protein from SAOS-p53 inducible cell lysate is purified from cells using GST-Mdm2 (5 pmol) pre-bound to GS beads. Samples are then incubated with test compounds as above. Subsequently 2 µl rabbit E1, 1 µl UbcH5b, and 10 µg of ubiquitin are added. After reaction for 15 min at 23° C., samples are subject to SDS-PAGE under reducing conditions, transferred to nitrocellulose membranes and immunoblotted with anti-p53 (DO-1) followed by ECL using standard techniques.

Example 8

E1 Inhibitor Interacts with Ubiquitin E1 Covalently

A number of the steps involved in regulating protein ubiquitination are known. Among those steps, the ubiquitin activating enzyme (E1) initially forms a high energy thioester linkage with ubiquitin. Ubiquitin is then transferred to a reactive cysteine residue of one of many ubiquitin conjugating enzymes known as Ubc or ubiquitin E2 enzymes.

Here, the interaction of the E1 inhibitor 4-[4-(5-nitro-furan-2-ylmethylene)-3,5-dioxo-pyrazolidin-1-yl]-benzoic acid methyl acid (designated as E1-41) with ubiquitin E1 was examined.

Figure 9:
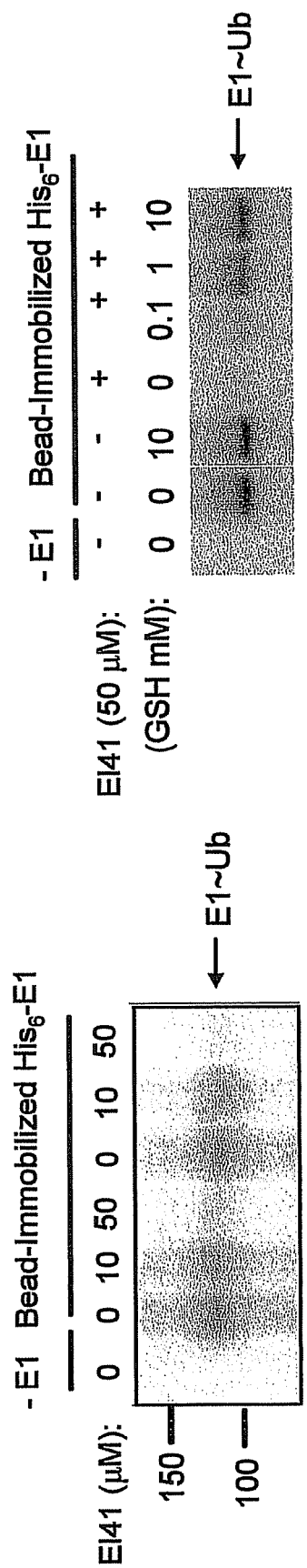
FIGS. 9A and 9B show that the E1 inhibitor 4-[4-(5-nitro-furan-2-ylmethylene)-3,5-dioxo-pyrazolidin-1-yl]-benzoic acid methyl acid interacts with ubiquitin E1 covalently.

Bead immobilized His$_6$-E1 was treated with E1 inhibitor 4-[4-(5-nitro-furan-2-ylmethylene)-3,5-dioxo-pyrazolidin-1-yl]-benzoic acid methyl acid (E1 41) at a range of concentrations (0-50 µm) as indicated in FIG. 9A. The beads were subjected to wash (+wash) or no wash (-wash) conditions. Panel A shows the results of protein blotting for ubiquitin E1 enzyme. In both the washed and unwashed conditions, identical band patterns of E1-Ub detection are seen, indicating that the E1 41 compound cannot be washed away. These results suggest that the E1 41 compound and ubiquitin E1 interact in a covalent manner.

The ability of a compound to inhibit E1 activity may come from the ability of the compound to interfere with the formation of thiolester linkages between ubiquitin and E1. Next, the biological activity of E1 41 was tested to examine if it can be inhibited or prevented by treatment with an excess of reduced glutathione. FIG. 9B shows the results of an experiment in which bead immobilized His$_6$-E1 was treated in the presence or absence of E1 inhibitor E1 41 (50 µM), and the presence or absence of glutathione (GSH) at a range of doses (0.1-10 mM). Panel B shows the results of protein blotting for ubiquitin E1 enzyme. The inhibitory action of E1 41 can be prevented by the addition of reduced glutathione (GSH) in a dose-dependent manner. Thus, E1 41 can act as a target for nucleophilic attack by active site thiol of E1 (e.g., a central double bond of a compound can serve as Michael-acceptor for the nucleophilic thiol in a Michael-type reaction). Taken together, the data indicates that E1 41 interacts with the ubiquitin E1 in a covalent manner.

Example 9

E1 Inhibitor Blocks IL-1 Induced Activation of NFκB

NFκB is a regulator of cell proliferation and survival. Accordingly, misregulation of NFκB plays a role in cancer and other proliferative diseases.

Here, the ability of 4-[4-(5-nitro-furan-2-ylmethylene)-3, 5-dioxo-pyrazolidin-1-yl]-benzoic acid methyl acid (E1-41) to prevent activation of NfκB in cells was tested.

Figure 10:
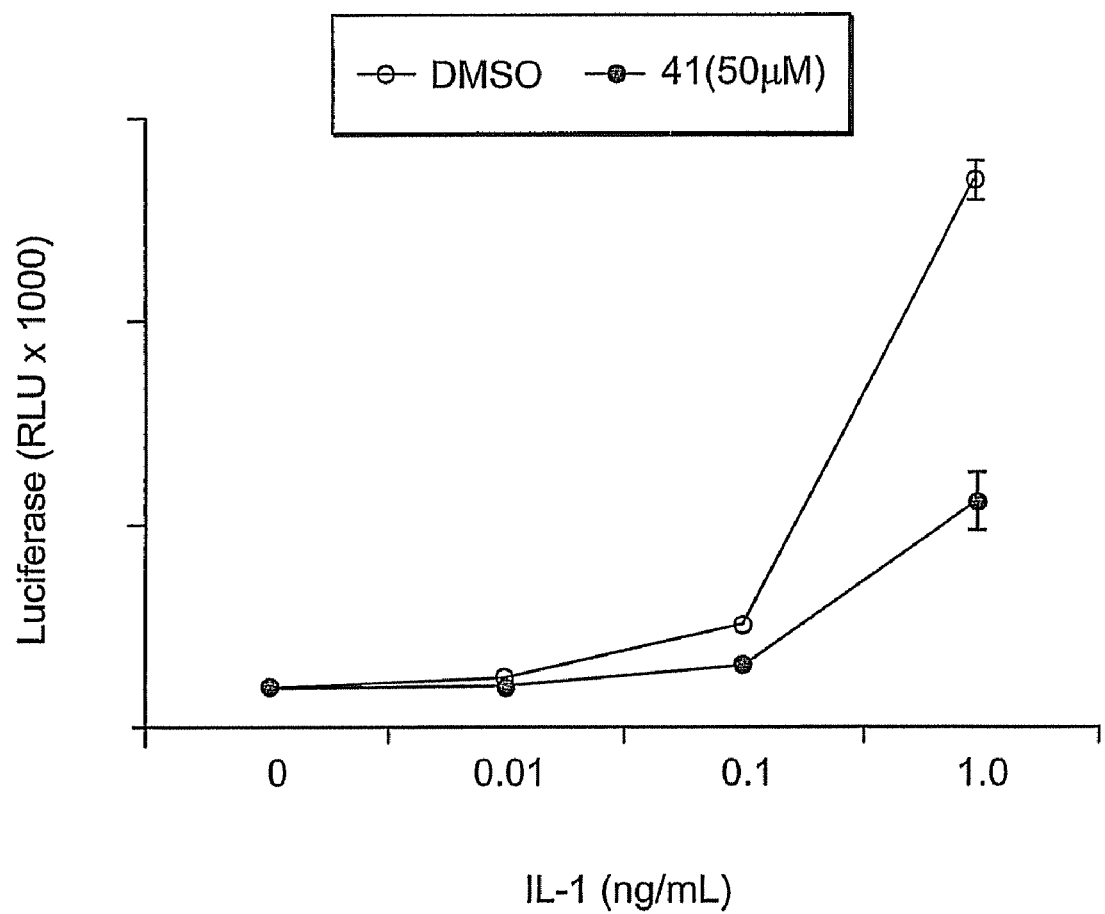
FIG. 10 shows that the E1 inhibitor 4-[4-(5-nitro-furan-2-ylmethylene)-3,5-dioxo-pyrazolidin-1-yl]-benzoic acid methyl acid blocks IL-1-induced activation of NFκB.

HeLa cells (human epithelial cells) were transfected with a NFκB response element-driven luciferase reporter. The cells were treated with E1 41 (50 μM) for 10 minutes, or dimethyl sulfoxide (DMSO) control. Interleukin 1 (IL-1) was added to the cells for 2 hours. IL-1 was added at concentrations ranging from 0-1.0 ng/ml to induce activation of NFκB. An assay for luciferase activity was carried out according to the methods as described in the commercially available PROMEGA system for luciferase detection. FIG. 10 shows that in cells treated with E1-41, there was a reduction of luciferase activity (RLU×1000), indicating that E1 41 blocked IL-1 induced activation of NFκB.

These results indicate that E1 41 is able to prevent activation of NFκB.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting inflammation in a mammal in need of treatment for an NF-κB-mediated inflammatory disease that is responsive to inhibition of ubiquitin E1 comprising:

administering to the subject an effective amount of one or more pyrazolidinyl compounds of Formula (I), or a pharmaceutically acceptable salt thereof:

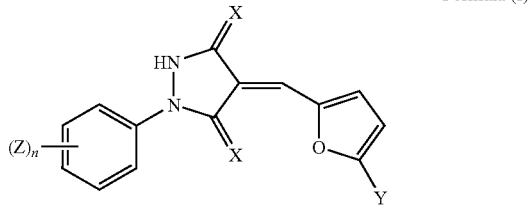

Formula (I)

wherein,
each X is O,
Y is $NO_2$,
n is 1, and
Z is halogen or $C(O)OR^3$, wherein $R^3$ is a $C_1$-$C_{12}$ straight or branched chain alkyl, wherein the NF-κB-mediated inflammatory disease is sepsis, arthritis, inflammatory myocarditis, glomerulonephritis, psoriasis, Lupus, asthma, lung fibrosis, atherosclerosis, autoimmune encephalomyelitis, cystic fibrosis, rheumatoid arthritis, or systemic inflammatory response syndrome.

2. The method of claim 1, wherein the pyrazolidinyl compound is 4-[4-(5-nitro-furan-2-ylmethylene)-3,5-dioxo-pyrazolidin-1-yl]-benzoic acid ethyl ester.

3. A method of inhibiting inflammation in a mammal in need of treatment for an NF-κB-mediated inflammatory disease that is responsive to inhibition of ubiquitin E1 comprising:

administering to the subject an effective amount of 4-[4-(5-nitro-furan-2-ylmethylene)-3,5-dioxo-pyrazolidin-1-yl]-benzoic acid ethyl ester, wherein the NF-κB-mediated inflammatory disease is sepsis, arthritis, inflammatory myocarditis, glomerulonephritis, psoriasis, Lupus, inflammatory conditions of the gastrointestinal tract, such as inflammatory bowel disease, ulcerative colitis, Crohn's Disease, inflammatory conditions of the central nervous system, asthma, lung fibrosis, atherosclerosis, autoimmune encephalomyelitis, cystic fibrosis, rheumatoid arthritis, or systemic inflammatory response syndrome.

* * * * *